United States Patent
Ohzawa

(10) Patent No.: US 8,582,717 B2
(45) Date of Patent: Nov. 12, 2013

(54) CONCENTRATION MEASURING METHOD AND FLUORESCENT X-RAY SPECTROMETER

(75) Inventor: Sumito Ohzawa, Kyoto (JP)

(73) Assignee: Horiba, Ltd. (JP)

( * ) Notice: Subject to any disclaimer, the term of this patent is extended or adjusted under 35 U.S.C. 154(b) by 452 days.

(21) Appl. No.: 12/940,223

(22) Filed: Nov. 5, 2010

(65) Prior Publication Data
US 2011/0103547 A1    May 5, 2011

(30) Foreign Application Priority Data
Nov. 5, 2009  (JP) .................................. 2009-254204

(51) Int. Cl.
  G01N 23/223   (2006.01)
  G01T 1/28     (2006.01)
  G01J 3/443    (2006.01)

(52) U.S. Cl.
  USPC .............................. 378/45; 378/48; 356/307

(58) Field of Classification Search
  USPC ........ 378/6, 7, 44, 45, 48, 49, 86, 98.12, 210, 378/901; 250/339.07, 339.09, 370.06, 250/370.08, 370.09; 356/300, 306, 307, 356/326
  See application file for complete search history.

(56) References Cited

U.S. PATENT DOCUMENTS

| | | | | |
|---|---|---|---|---|
| 3,375,369 A | * | 3/1968 | Goldman et al. | 378/49 |
| 4,577,338 A | * | 3/1986 | Takahashi et al. | 378/48 |
| 2010/0091944 A1 | * | 4/2010 | Oki et al. | 378/45 |

FOREIGN PATENT DOCUMENTS

JP   2001-91481 A   4/2001

OTHER PUBLICATIONS

W.H. McMaster et al., "Compilation of X-Ray Cross Sections", Lawrence Radiation Laboratory, UCRL-50174 Sec. II Rev. 1.

* cited by examiner

*Primary Examiner* — Anastasia Midkiff
(74) *Attorney, Agent, or Firm* — Cantor Colburn LLP

(57) ABSTRACT

In the present invention, a fluorescent X-ray analysis is made for a sample such as a liquid fuel including an object component such as sulfur. A background related to scattered X-rays and a system peak is subtracted from a fluorescent X-ray intensity of the object component, which is obtained from a spectrum acquired by the fluorescent X-ray analysis. A correction corresponding to the composition of the sample is performed for the fluorescent X-ray intensity obtained by subtracting the background. A calibration curve representing the relation between a value, which is obtained after performing the correction for the fluorescent X-ray intensity obtained by subtracting the background, and a concentration of the object component is preset. The concentration of the object component in the sample is calculated on the basis of the calibration curve.

5 Claims, 8 Drawing Sheets

F I G. 3
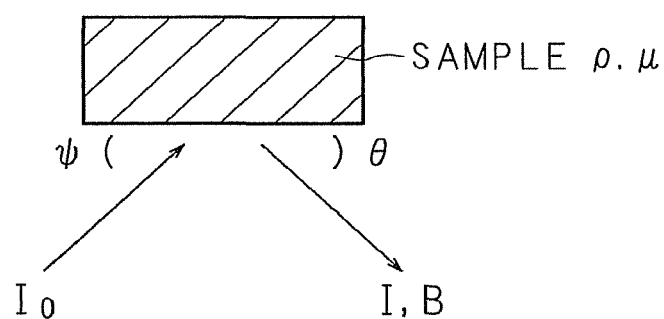

FIG. 4A

| | FOSSIL FUEL | ETHANOL 15% | ETHANOL 50% | ETHANOL 85% | ETHANOL 100% |
|---|---|---|---|---|---|
| μ(2.3keV) | 178.373 | 191.362 | 221.671 | 251.979 | 264.968 |
| μ(4.5keV) | 22.360 | 24.192 | 28.466 | 32.740 | 34.572 |

FIG. 4B

| | FOSSIL FUEL | ETHANOL 15% | ETHANOL 50% | ETHANOL 85% | ETHANOL 100% |
|---|---|---|---|---|---|
| a | -3.094 | -3.081 | -3.058 | -3.041 | -3.034 |
| b | 7.761 | 7.821 | 7.948 | 8.062 | 8.107 |

CONCENTRATION MEASURING METHOD AND FLUORESCENT X-RAY SPECTROMETER

CROSS-REFERENCE TO RELATED APPLICATIONS

This Nonprovisional application claims priority under 35 U.S.C. §119(a) on Patent Application No. 2009-254204 filed in Japan on Nov. 5, 2009, the entire contents of which are hereby incorporated by reference.

BACKGROUND

1. Technical Field

The present invention relates to fluorescent X-ray analysis. More specifically, the present invention relates to a concentration measuring method and a fluorescent X-ray spectrometer for measuring the concentration of a measurement object, such as sulfur, included in a sample, e.g. an alcohol fuel such as methanol or ethanol, using fluorescent X-ray analysis.

2. Description of Related Art

Fluorescent X-ray analysis is an analytical method for irradiating a sample with primary X-rays, detecting fluorescent X-rays generated from the sample and making a qualitative analysis or a quantitative analysis of elements contained in the sample on the basis of a spectrum of the fluorescent X-rays. A fluorescent X-ray spectrometer for making a fluorescent X-ray analysis is composed of; an X-ray tube for generating primary X-rays; an X-ray detector constituted of a semiconductor detector, a proportional counter or the like; an analyzer for analyzing the wavelength distribution or the energy distribution of X-rays detected by the X-ray detector; and the like. For making a fluorescent X-ray analysis, a sample is irradiated with primary X-rays generated by the X-ray tube, fluorescent X-rays generated from the sample irradiated with the primary X-rays are detected by the X-ray detector, and a spectrum of the detected fluorescent X-rays is analyzed by the analyzer.

Such fluorescent X-ray analysis can be used for measuring the concentration of impurities included in a liquid fuel. For example, the concentration of sulfur in a liquid fuel is measured using fluorescent X-ray analysis with the aim of reduction in sulfur, which is a hazardous component, included in a liquid fuel such as a diesel fuel. When a fluorescent X-ray analysis is made for a sample of a liquid fuel including sulfur, an X-ray spectrum including a signal of fluorescent X-rays of sulfur and a signal of scattered X-rays, which are primary X-rays scattered in the sample, is obtained. When the fluorescent X-ray intensity of sulfur to be obtained from the spectrum is denoted by S and the scattered X-ray intensity is denoted by B, a value (S/B) to be obtained by dividing S by B becomes a function approximately proportional to the concentration of sulfur in the sample. A calibration curve representing the relation between (S/B) and the concentration is preset using a standard sample having a known sulfur concentration. The sulfur concentration can be obtained by comparing the value of (SIB), which is obtained by a fluorescent X-ray analysis of a sample having an unknown sulfur concentration, with the calibration curve.

In recent years, standards for the regulation of hazardous components included in a liquid fuel such as gas oil has been getting strict and it is required to measure a low sulfur concentration. In such a case, it is required to obtain the sulfur concentration from weaker fluorescent X-rays. A spectrum to be obtained from a fluorescent X-ray analysis includes a peak, which is referred to as a system peak. A system peak is a peak attributed to: X-rays scattered in the air in a fluorescent X-ray spectrometer; X-rays reflected at components in the fluorescent X-ray spectrometer; fluorescent X-rays generated by irradiation of components in a fluorescent X-ray spectrometer with X-rays; or the like, and is dependent on a fluorescent X-ray spectrometer. When a low sulfur concentration is to be measured, a signal of fluorescent X-rays of sulfur is small. Therefore, the effect of the system peak superimposed on a signal of fluorescent X-rays of sulfur becomes large and the value of (S/B) becomes unproportional to the concentration. In view of the facts, Japanese Patent Application Laid-Open No. 2001-91481 discloses a technique for measuring a low sulfur concentration in the presence of a system peak, by preliminarily obtaining a calibration curve designed in consideration of the effect of the system peak and measuring the sulfur concentration using the obtained calibration curve.

SUMMARY

In recent years, use of a new type of a liquid fuel such as ethanol or bio gasoline, which is widely different in composition from a conventional liquid fuel, has started in addition to use of a conventional liquid fuel such as a diesel fuel or gasoline. When the composition of a sample changes, the mass absorption coefficient of X-rays also changes, causing a change in the fluorescent X-ray intensity and the scattered X-ray intensity. For example, the fluorescent X-ray intensity and the scattered X-ray intensity of sulfur change when the composition of a sample changes, even when the concentration of sulfur in the sample is constant. Regarding a conventional liquid fuel having a mass absorption coefficient which does not fluctuate greatly, the relation between the fluorescent X-ray intensity of sulfur and the sulfur concentration can be represented by a calibration curve regardless of the sample. On the other hand, regarding a new type of a liquid fuel having a mass absorption coefficient which differs widely from conventional one, the relation between the fluorescent X-ray intensity of sulfur and the sulfur concentration does not fit a conventional calibration curve. Accordingly, it is impossible to make a precise measurement of the concentration of sulfur in a new type of a liquid fuel. It is required to obtain a calibration curve one by one for each composition of a liquid fuel in order to measure the concentration of sulfur in a new type of a liquid fuel. To obtain a calibration curve one by one has a problem in feasibility.

The present invention has been made in view of such a situation, and the object thereof is to provide a concentration measuring method and a fluorescent X-ray spectrometer, which can measure the concentration of a measurement object in a sample using fluorescent X-ray analysis even for a sample having a different composition by: correcting a fluorescent X-ray intensity in view of a difference in a mass absorption coefficient of X-rays due to a difference in the composition of a sample; preliminarily obtaining a calibration curve; and calculating the concentration from the corrected fluorescent X-ray intensity and the calibration curve.

A concentration measuring method according to the present invention is a concentration measuring method for irradiating a sample with primary X-rays, acquiring a spectrum of secondary X-rays generated from the sample, obtaining, a fluorescent X-ray intensity of an object component included in the sample from the spectrum and measuring a concentration of an object component in a sample from the obtained fluorescent X-ray intensity by means of a fluorescent X-ray spectrometer, characterized by comprising steps of: subtracting a background, which is related to scattered X-rays included in the secondary X-rays and a signal specific to the fluorescent X-ray spectrometer, from the fluorescent X-ray intensity of the object component obtained from the acquired spectrum; performing a correction corresponding to a composition of the sample for the fluorescent X-ray intensity obtained by subtracting the background; and calculating a concentration of the object component in the sample on the basis of a calibration curve representing a relation between a concentration of the object component and a value obtained after performing the correction for the fluorescent X-ray intensity obtained by subtracting the background.

A concentration measuring method according to the present invention is characterized by comprising steps of: acquiring spectrums of secondary X-rays generated from a plurality of standard samples, concentrations of the object component of which are zero and compositions of which are different from each other; and setting a subtraction formula for subtracting the background from a fluorescent X-ray intensity of the object component, using fluorescent X-ray intensities and scattered X-ray intensities of the object component, which are obtained from the spectrums acquired for a plurality of standard samples.

A concentration measuring method according to the present invention is characterized by comprising steps of setting a subtraction formula by calculating constants $\alpha$ and $\beta$ according to a plurality of formulas obtained by setting I=0 and assigning S and B, which are obtained from the spectrums acquired for a plurality of standard samples, to a subtraction formula I=S−$\alpha$×B−$\beta$ (wherein I: a fluorescent X-ray intensity obtained by subtracting the background, S: a fluorescent X-ray intensity of the object component obtained from a spectrum, $\alpha$ and $\beta$: constants, and B: a scattered X-ray intensity obtained from a spectrum) for subtracting the background from the fluorescent X-ray intensity of the object component, which is obtained from a spectrum; and subtracting the background from the fluorescent X-ray intensity of the object component by assigning S and B, which are obtained from an acquired spectrum, to a subtraction formula in which calculated values are set as $\alpha$ and $\beta$.

A concentration measuring method according to the present invention is characterized by comprising steps of: acquiring spectrums of secondary X-rays generated from a plurality of standard samples, concentrations of the object component of which have known values that are not zero; subtracting the background from fluorescent X-ray intensities of the object component, which are obtained from the spectrums acquired for a plurality of standard samples; and setting a correction formula for performing the correction, on the basis of a relation between concentrations of the object component related to a plurality of standard samples and fluorescent X-ray intensities obtained by subtracting the background.

A concentration measuring method according to the present invention is characterized by comprising steps of: setting a correction formula I×$(B_0/B)^\gamma$ by calculating a constant $\gamma$ according to a plurality of formulas obtained by assigning $I_k$, $B_0$ and $B_k$ to a relation formula (wherein $I_k$: a value obtained by subtracting the background from a fluorescent X-ray intensity of an object component obtained from a spectrum related to a k-th standard sample, $B_0$: a scattered X-ray intensity obtained from a spectrum related to a specific reference sample to be a reference of a fluorescent X-ray intensity, $B_k$: a scattered X-ray intensity obtained from a spectrum related to the k-th standard sample, and $\gamma$: a constant) expressing that a concentration $C_k$ of the object component related to the k-th standard sample is proportional to $I_k \times (B_0/B_k)^\gamma$; and performing the correction by assigning I and B to a correction formula in which a calculated value is set as $\gamma$.

A concentration measuring method according to the present invention is characterized by comprising steps of: acquiring spectrums of secondary X-rays generated from a plurality of standard samples, concentrations of the object component of which have known values that are different from each other; subtracting the background from fluorescent X-ray intensities of the object component obtained from a plurality of acquired spectrums; performing the correction for values obtained by subtracting the background from fluorescent X-ray intensities related to a plurality of standard samples; and obtaining a calibration curve representing a relation between a concentration of the object component in the sample and a value obtained after performing the correction for the fluorescent X-ray intensity obtained by subtracting the background, on the basis of concentrations of the object component related to a plurality of standard samples and values obtained after performing the correction for values obtained by subtracting the background from fluorescent X-ray intensities related to a plurality of standard samples.

A fluorescent X-ray spectrometer according to the present invention is a fluorescent X-ray spectrometer, which includes an irradiating unit for irradiating a sample with primary X-rays, an acquiring unit for acquiring a spectrum of secondary X-rays generated from the sample and an obtaining unit for obtaining a fluorescent X-ray intensity of an object component included in the sample from the spectrum, for calculating a concentration of the object component in the sample on the basis of the fluorescent X-ray intensity obtained by the obtaining unit, characterized by comprising: a subtraction formula storing unit for storing a subtraction formula for subtracting a background, which is related to scattered X-rays included in the secondary X-rays and a signal specific to the fluorescent X-ray spectrometer, from the fluorescent X-ray intensity of the object component obtained by the obtaining unit from the spectrum acquired by the acquiring unit; a correction formula storing unit for storing a correction formula for performing a correction corresponding to a composition of the sample for the fluorescent X-ray intensity obtained by subtracting the background; a calibration curve storing unit for storing a calibration curve representing a relation between a concentration of the object component and a value obtained after performing the correction for the fluorescent X-ray intensity obtained by subtracting the background; a subtracting unit for subtracting the background from the fluorescent X-ray intensity of the object component, which is obtained by the obtaining unit from the spectrum acquired by the acquiring unit, using the subtraction formula; a correction unit for performing the correction for the fluorescent X-ray intensity, which is obtained by subtracting the background, using the correction formula; and a concentration calculating unit for calculating a concentration of the object component in the sample on the basis of the calibration curve.

In the present invention, a fluorescent X-ray analysis is made for a sample such as a liquid fuel including an object component such as sulfur. A background related to scattered X-rays and a system peak specific to a fluorescent X-ray spectrometer is subtracted from a fluorescent X-ray intensity of the object component to be obtained from a spectrum acquired by a fluorescent X-ray analysis. A correction corresponding to the composition of the sample is performed for the fluorescent X-ray intensity obtained by subtracting the background. The concentration of the object component in the sample is calculated on the basis of a calibration curve representing the relation between a value obtained after performing the correction and the concentration of the object component.

Moreover, in the present invention, a fluorescent X-ray analysis is made for a plurality of standard samples, the concentrations of the object component of which are zero and the compositions of which are different from each other. A subtraction formula for subtracting a background from a fluorescent X-ray intensity is set using the fluorescent X-ray intensity of the object component and the scattered X-ray intensity obtained from the spectrum. In the measurement of the concentration, the background is subtracted from a fluorescent X-ray intensity, using the subtraction formula. By subtracting the background from the fluorescent X-ray intensity of the object component, it becomes possible to measure the concentration of an object component included even in a sample, the concentration of the object component of which is low.

Moreover, in the present invention, a fluorescent X-ray analysis is made for a plurality of standard samples, the concentrations of the object component of which have known values that are not zero. A correction formula for performing a correction of a fluorescent X-ray intensity corresponding to the composition of a sample is set on the basis of the relation between the concentration of the object component and the fluorescent X-ray intensity obtained by subtracting the background. In the measurement of the concentration, a correction using the correction formula is performed for the fluorescent X-ray intensity obtained by subtracting the background. Since a correction corresponding to the composition of a sample is performed for a value obtained by subtracting the background from the fluorescent X-ray intensity of the object component, a value corresponding to the concentration of the object component can be obtained independently of the composition of the sample.

Moreover, in the present invention, a fluorescent X-ray analysis is made for a plurality of standard samples, the concentrations of the object component of which have known values. A calibration curve representing the relation between the concentration of the object component and a value obtained after performing the correction for the fluorescent X-ray intensity obtained by subtracting the background is preliminarily created. In the measurement of the concentration, the concentration of the object component is calculated using the calibration curve.

In the present invention, a background is subtracted from a fluorescent X-ray intensity of the object component, which is obtained from a spectrum acquired by a fluorescent X-ray analysis. Furthermore, a correction of a fluorescent X-ray intensity corresponding to the composition of a sample is performed. With such a manner, a value corresponding to the concentration of the object component can be obtained independently of the composition of the sample. Accordingly, it is unnecessary to create a calibration curve for each sample, the composition of which is different, and it is possible to make a high-precision measurement of the concentration of an object component in a sample having any composition using a fluorescent X-ray analysis. Especially, the present invention makes it possible to make a high-precision measurement of the concentration of a hazardous component in various liquid fuels including a new type of a liquid fuel such as ethanol or bio gasoline, and the present invention can be used for reducing a hazardous component in a liquid fuel. As described above, the present invention provides beneficial effects.

The above and further objects and features will more fully be apparent from the following detailed description with accompanying drawings.

BRIEF DESCRIPTION OF THE SEVERAL VIEWS OF THE DRAWINGS

FIG. 3 is a schematic view for illustrating a situation where a fluorescent X-ray analysis is made;

FIGS. 4A and 4B are diagrams for illustrating the result of evaluation of mass absorption coefficients and evaluation of constants a and b for samples including a fossil fuel and ethanol mixed therein;

DETAILED DESCRIPTION

The following description will explain the present invention in concrete terms with reference to the drawings illustrating an embodiment thereof.

Figure 1:
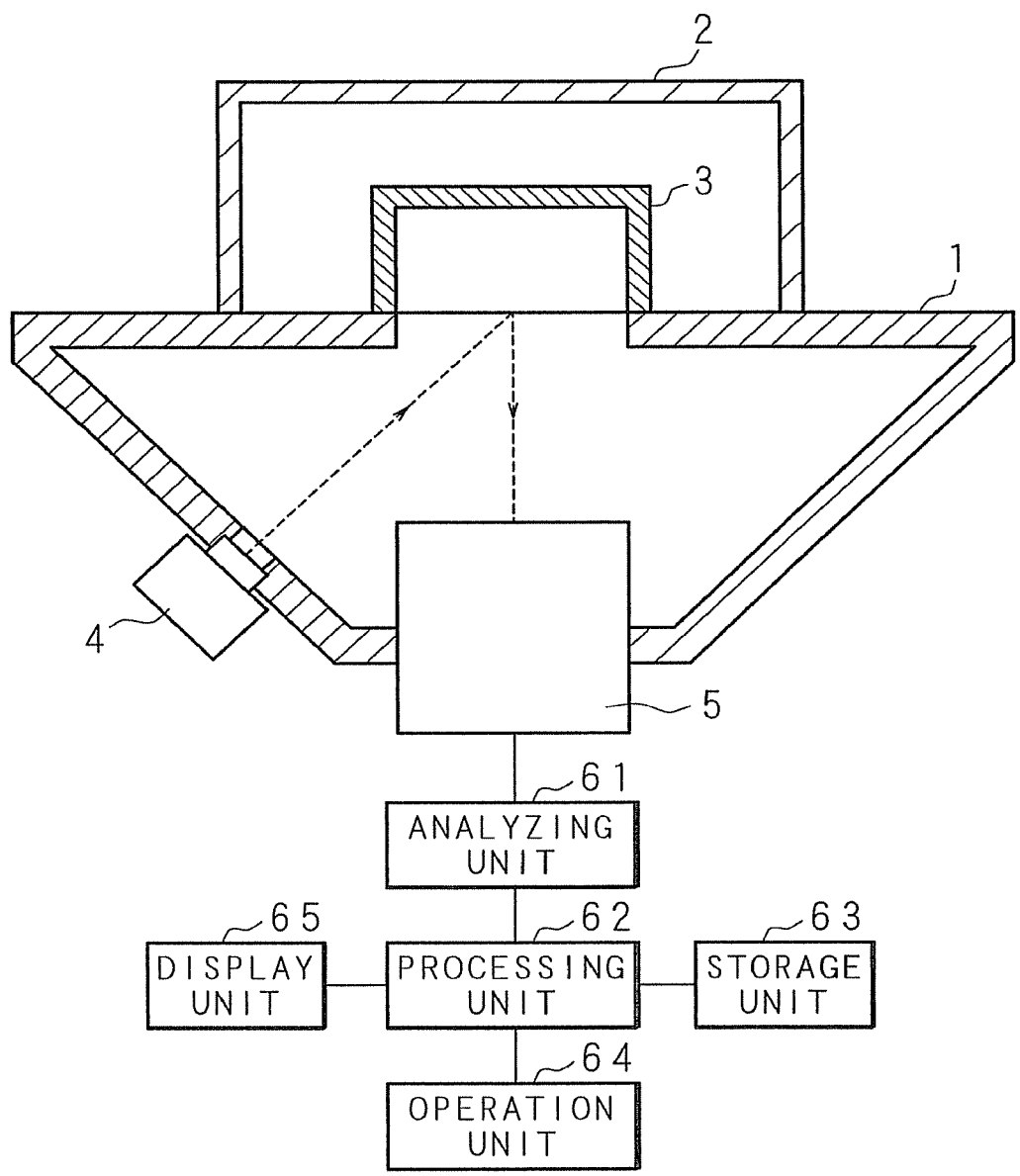
FIG. 1 is a schematic view for illustrating the structure of a fluorescent X-ray spectrometer according to the present invention.

FIG. 1 is a schematic view for illustrating the structure of a fluorescent X-ray spectrometer according to the present invention. The fluorescent X-ray spectrometer is provided with a housing 1, which is formed in a box shape from a material for blocking X-rays out. An upper part of the housing 1 constitutes a flat face. An opening is formed at an upper part of the housing 1. A sample cell 3 for holding a sample to be analyzed is laid in the opening. The fluorescent X-ray spectrometer is also provided with a cover 2 for covering at least a part of the upper face of the housing 1 including the opening. The sample cell 3 is covered with the cover 2. The sample cell 3 is a cell for holding powder or a fluid sample such as a liquid fuel.

Inside the housing 1, a hollow measurement chamber is formed. The housing 1 is provided with an X-ray tube 4 for emitting primary X-rays into the measurement chamber and an X-ray detector 5. The X-ray tube 4 is constructed to generate primary X-rays by causing collision of accelerated electrons against a target. In the present embodiment, the material of the target of the X-ray tube 4 is titanium and the excitation voltage is 8 keV. Here, the energy of the peak of primary X-rays is 4.5 keV. It is to be noted that the X-ray tube 4 may be constructed to have a target made of a different material and have a different excitation voltage. The X-ray tube 4 is placed at a position to irradiate the opening of the housing 1 with primary X-rays. Since the sample cell 3 is placed at the position of the opening of the housing 1, the sample in the sample cell 3 is irradiated with primary X-rays generated from the X-ray tube 4 for making a fluorescent X-ray analysis. The sample in the sample cell 3 irradiated with primary X-rays generates secondary X-rays, and the secondary X-rays are emitted into the measurement chamber. The secondary X-rays include: fluorescent X-rays attributed to components of the sample; and scattered X-rays, which are primary X-rays scattered in the sample. The X-ray detector 5 is placed at a position to detect secondary X-rays generated from the sample in the sample cell 3. The path of primary X-rays from the X-ray tube 4 and the path of secondary X-rays to be detected by the X-ray detector 5 are indicated by arrows drawn by a broken line in FIG. 1. The X-ray detector 5 is constructed by using a proportional counter as a detecting element and outputs electric signals proportional to the energy of secondary X-rays entering the proportional counter. It is to be noted that an embodiment of the X-ray detector 5 may use a detecting element other than a proportional counter, e.g., a semiconductor detector.

The X-ray detector 5 is connected with an analyzing unit 61 for analyzing electric signals outputted from the X-ray detector 5. The analyzing unit 61 receives electric signals outputted from the X-ray detector 5, measures intensities of respective electric signals corresponding to the energy of secondary X-rays and counts the number thereof. The analyzing unit 61 then performs a process for acquiring the relation between the energy of secondary X-rays and the number of counts, i.e., a spectrum of secondary X-rays. The analyzing unit 61 is connected with a processing unit 62 for executing processes for a concentration measuring method of the present invention using the spectrum acquired by the analyzing unit 61. The processing unit 62 is composed of: a computing unit for executing computation; a RAM for storing temporary data associated with computation; a ROM for storing a program for executing processes for a concentration measuring method of the present invention; and the like. The processing unit 62 also executes a process for controlling the actions of the X-ray tube 4, the X-ray detector 5 and the analyzing unit 61. The processing unit 62 is connected with: a nonvolatile storage unit 63; an operation unit 64, through which the user enters various kinds of instructions; and a display unit 65 for displaying information to be used for operation.

Figure 2:
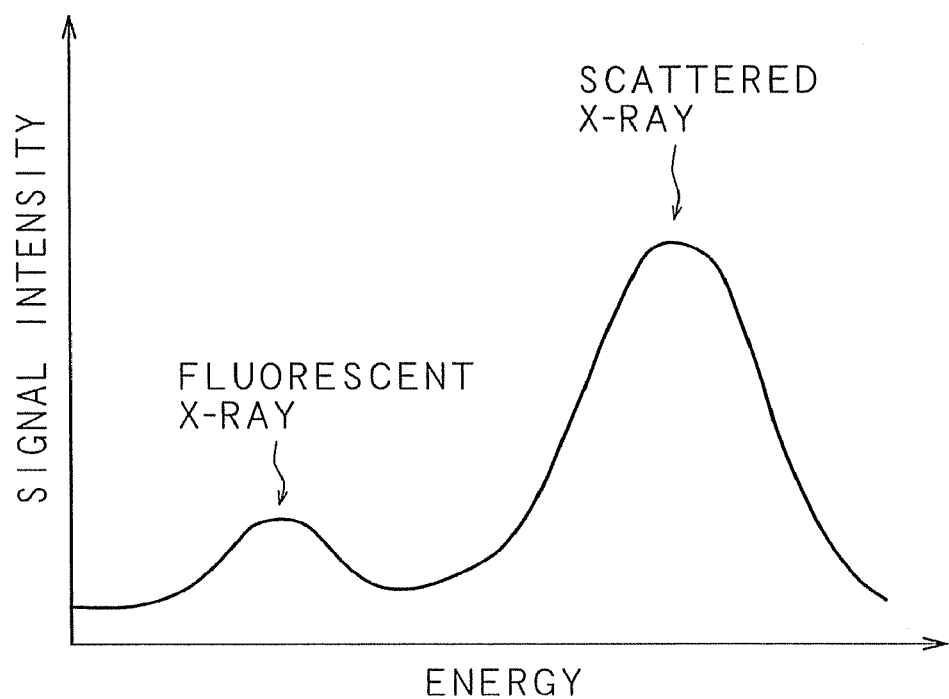
FIG. 2 is a schematic view for illustrating an example of a spectrum of secondary X-rays.

Next, the principle of a concentration measuring method of the present invention will be explained. In the present embodiment, an example wherein a liquid fuel such as a diesel fuel or ethanol is used as a sample and sulfur is specified as an object component will be explained. FIG. 2 is a schematic view for illustrating an example of a spectrum of secondary X-rays. The spectrum includes a signal related to scattered X-rays and a signal related to fluorescent X-rays generated by excitation of sulfur in the sample, which is caused by primary X-rays. The energy of the peak of the signal related to scattered X-rays is 4.5 keV, and the energy of the peak of the signal related to fluorescent X-rays of sulfur is 2.3 keV. Impurities such as sulfur are preliminarily removed from a liquid fuel, which is a sample, by purification. Therefore, the concentration of sulfur in the sample is low and the signal related to fluorescent X-rays of sulfur is smaller than the signal related to scattered X-rays. The fluorescent X-ray intensity of sulfur can be obtained by measuring the size of the peak of the signal related to fluorescent X-rays of sulfur or by integrating the signal related to fluorescent X-rays of sulfur.

However, the bottom part of the signal of scattered X-rays and a system peak are superimposed on the signal of fluorescent X-rays included in the spectrum, and the fluorescent X-ray intensity to be obtained from the spectrum includes a background related to scattered X-rays and the system peak. The system peak is a peak to be included in the spectrum by detection of X-rays other than scattered X-rays and fluorescent X-rays from the samples, such as X-rays scattered in the air in the fluorescent X-ray spectrometer; X-rays reflected at components of the fluorescent X-ray spectrometer; or fluorescent X-rays generated from components of the fluorescent X-ray spectrometer, by the X-ray detector 5. The system peak is dependent on the structure of a fluorescent X-ray spectrometer and has a quantity specific to an individual fluorescent X-ray spectrometer. When a scattered X-ray intensity, which can be obtained by measuring the size of the peak of the signal related to scattered X-rays or integrating the signal related to scattered X-rays, is denoted by B, a background related to scattered X-rays included in the fluorescent X-ray intensity of an object component can be expressed as $\alpha \times B$ using a constant $\alpha$. Moreover, a background related to the system peak included in the fluorescent X-ray intensity can be expressed by a constant $\beta$. Accordingly, when a fluorescent X-ray intensity of sulfur to be obtained from the spectrum is denoted by S and a value obtained by subtracting a background from the fluorescent X-ray intensity of sulfur is denoted by I, I can be expressed by the following formula (1).

$$I = S - \alpha \times B - \beta \tag{1}$$

A background can be subtracted from the fluorescent X-ray intensity of sulfur by using the formula (1). The constants $\alpha$ and $\beta$ included in the formula (1) can be calculated from the result of a fluorescent X-ray analysis of a plurality of standard samples, the concentrations of an object component (sulfur in the present embodiment) of which are zero and the compositions of which are different from each other. A fluorescent X-ray analysis is made for a first standard sample and a second standard sample, the sulfur contents of which are zero, to acquire a spectrum of secondary X-rays for each sample. For example, the first standard sample is a diesel fuel and the second standard sample is ethanol. The fluorescent X-ray intensity of sulfur to be obtained by a fluorescent X-ray analysis of the first standard sample will be denoted by S1, and the scattered X-ray intensity to be obtained by the fluorescent X-ray analysis will be denoted by B1. The fluorescent X-ray intensity of sulfur to be obtained by a fluorescent X-ray analysis of the second standard sample will be denoted by S2, and the scattered X-ray intensity to be obtained by the fluorescent X-ray will be denoted by B2. The following two formulas can be obtained by assigning S1, B1, S2 and B2 to the formula (1).

$$0 = S1 - \alpha \times B1 - \beta$$

$$0 = S2 - \alpha \times B2 - \beta$$

Since the sulfur concentration is zero, a value I to be obtained by subtracting a background from a fluorescent X-ray intensity of sulfur is zero. From the above formulas, the following formulas (2) and (3) can be obtained. Using the formulas (2) and (3), $\alpha$ and $\beta$ can be calculated. The formula (1) in which $\alpha$ and $\beta$ are set is a subtraction formula according to the present invention. It is to be noted that $\alpha$ and $\beta$ may be calculated by the method of least squares, using three or more standard samples.

$$\alpha = \frac{S1 - S2}{B1 - B2} \tag{2}$$

$$\beta = \frac{S2 \times B1 - S1 \times B2}{B1 - B2} \tag{3}$$

When the composition of the sample changes, the density and the mass absorption coefficient of X-rays also change, causing a change in the fluorescent X-ray intensity and the scattered X-ray intensity. For example, the fluorescent X-ray intensity of sulfur and the scattered X-ray intensity change when the composition of the sample changes, even when the concentration of sulfur in the sample is constant. Accordingly, it is necessary to further perform a correction corresponding to the composition of the sample for a value obtained by subtracting a background from a fluorescent X-ray intensity using the formula (1), in order to compare fluorescent X-ray intensities of samples having different compositions.

FIG. 3 is a schematic view for illustrating a situation where a fluorescent X-ray analysis is made. The energy will be denoted by E; the intensity of primary X-rays, with which a sample is to be irradiated, will be denoted by $I_0(E)$; the incident angle of primary X-rays to the sample will be denoted by $\psi$; the output angle of secondary X-rays from the sample to the X-ray detector 5 will be denoted by $\theta$; the density of the sample will be denoted by $\rho$; and the mass absorption coefficient of X-rays at the sample will be denoted by $\mu(E)$. The mass absorption coefficient $\mu(E)$ is a quantity, which varies with the composition of a sample and changes with the energy of X-rays. The fluorescent X-ray intensity I of sulfur to be detected by the X-ray detector 5 can be expressed by the following formula (4). Here, I is a value which does not include a background.

$$I = \int_{absorption\ end}^{8keV} \frac{A_1 \cdot I_0(E)}{\rho\left(\frac{\mu(4.5\ keV)}{\sin\psi} + \frac{\mu(2.3\ keV)}{\sin\theta}\right)} dE \qquad (4)$$
$$= \frac{A_1}{\rho\left(\frac{\mu(4.5\ keV)}{\sin\psi} + \frac{\mu(2.3\ keV)}{\sin\theta}\right)} \int_{absorption\ end}^{8keV} I_0(E)\,dE$$

$A_1$ in the formula (4) denotes the excitation efficiency of sulfur, which is a constant. An absorption end in the formula (4) denotes the absorption end of sulfur, and sulfur does not absorb X-rays having energy lower than the absorption end. Moreover, 8 keV denotes the excitation voltage at the X-ray tube 4 as described above, 4.5 keV denotes the energy of the peak of primary X-rays, and $\mu(4.5\ keV)$ denotes the mass absorption coefficient of a sample for X-rays having energy of 4.5 keV. Said values will be different corresponding to the structure of the X-ray tube 4 when the structure of the X-ray tube 4 is different from that of the present embodiment. Moreover, 2.3 keV in the formula (4) denotes the energy of the peak of fluorescent X-rays of sulfur, and $\mu(2.3\ keV)$ denotes the mass absorption coefficient of a sample for X-rays having energy of 2.3 keV. Said values will vary with an object component when the object component is different from sulfur. Furthermore, a scattered X-ray intensity B to be detected by the X-ray detector 5 can be expressed by the following formula (5).

$$B = \frac{A_2 \cdot I_0(E)}{\rho\left(\frac{1}{\sin\psi} + \frac{1}{\sin\theta}\right)\mu(4.5\ keV)} \qquad (5)$$

$A_2$ in the formula (5) denotes the scattering efficiency of X-rays having energy of 4.5 keV, which is a constant. The formula (5) is obtained since primary X-rays and scattered X-rays have equal energy. It is found from the formulas (4) and (5) that the fluorescent X-ray intensity I obtained by subtracting a background is proportional to 1/(density×mass absorption coefficient). Accordingly, when the density of a single reference sample is denoted by $\rho_0$ and the mass absorption coefficient is denoted by $\mu_0$, a correction corresponding to the composition of a sample can be performed for the value I, which is obtained by subtracting a background from the fluorescent X-ray intensity of sulfur included in a sample having a density of $\rho$ and a mass absorption coefficient of $\mu$, using the following expression (6). The correction using the expression (6) is a correction to convert a fluorescent X-ray intensity obtained from a sample into a fluorescent X-ray intensity, which is to be obtained when the composition is the same as that of the reference sample.

$$I \times \frac{\rho \cdot \mu(2.3\ keV)}{\rho_0 \cdot \mu_0(2.3\ keV)} \qquad (6)$$

The result of measurement of the relation between the energy of X-rays and the mass absorption coefficient for various kinds of elements are described in "COMPILATION OF X-RAY CROSS SECTIONS," Lawrence Radiation Laboratory, UCRL-50174 Sec. II Rev. 1 (which will be hereinafter referred to as Known Document 1). As described in the Known Document 1, carbon and oxygen respectively have linear relations between the energy of X-rays and the mass absorption coefficient in a double logarithmic chart, which has an abscissa axis representing the energy of X-rays using keV as a unit and an ordinate axis representing the mass absorption coefficient, within the range of the energy of X-rays from 2.3 keV to 4.5 keV. The mass absorption coefficient of hydrogen is smaller than that of carbon and oxygen by four orders of magnitude or more, and is negligible compared with the mass absorption coefficients of carbon and oxygen. A liquid fuel such as a diesel fuel or ethanol to be used as a sample in the present embodiment contains carbon, oxygen and hydrogen as major ingredients. Since carbon and oxygen respectively have linear relations between the mass absorption coefficient and the energy of X-rays in a double logarithmic chart and the mass absorption coefficient of hydrogen is negligible, a sample has a linear relation between the mass absorption coefficient and the energy of X-rays in a double logarithmic chart. Accordingly, $\ln(\mu)=a\times\ln(E)+b$ is satisfied for a sample having an absorption coefficient of $\mu$, wherein a and b are unknown constants. Here, a slope a and an intercept b vary with samples.

Figure 5:
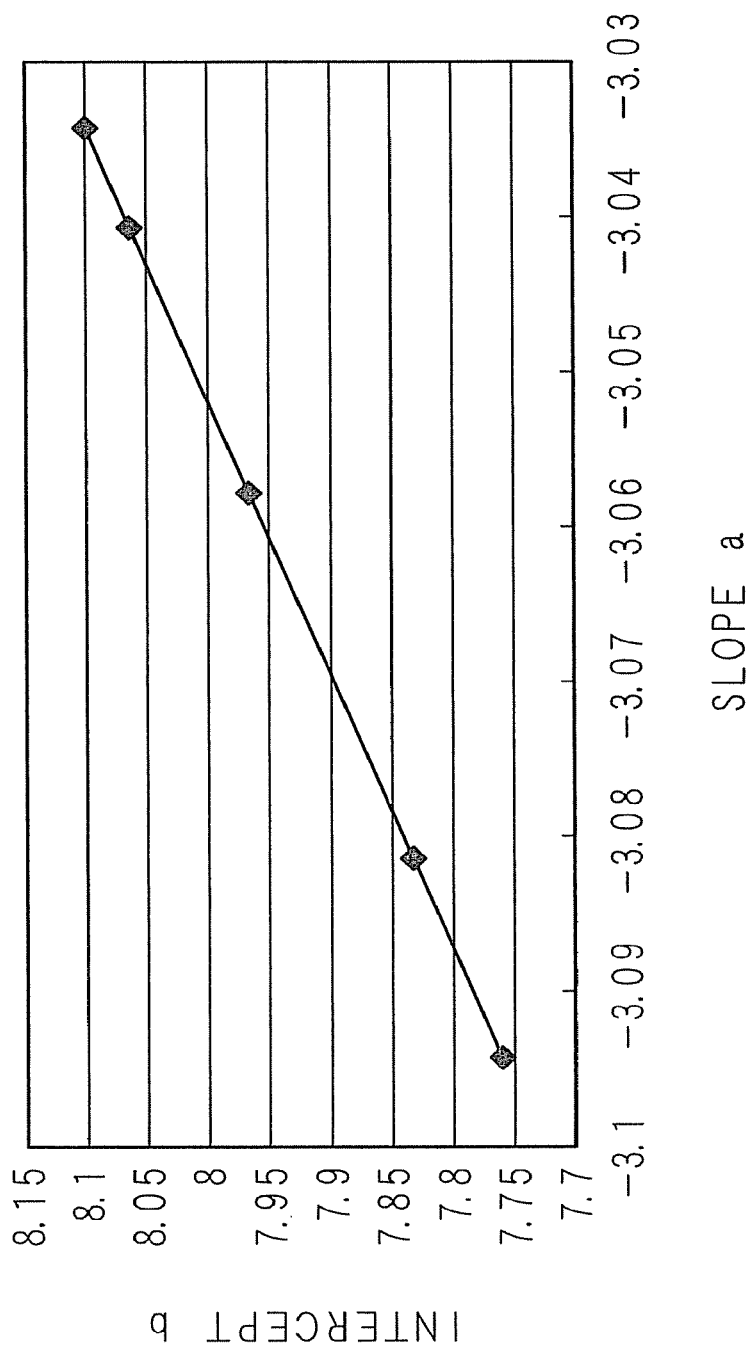
FIG. 5 is a characteristic diagram for illustrating the relation between constants a and b, which are calculated.

Here, the relation of the mass absorption coefficient with constants a and b for a sample including a fossil fuel such as a diesel fuel and ethanol mixed therein is evaluated. Used samples including a fossil fuel and ethanol mixed therein are: a sample including only a fossil fuel; a sample with 15% ethanol; a sample with 50% ethanol; a sample with 85% ethanol; and a sample with 100% ethanol. First, a mass absorption coefficient is obtained for each sample. FIGS. 4A and 4B are diagrams for illustrating the result of evaluation of mass absorption coefficients and evaluation of constants a and b for samples including a fossil fuel and ethanol mixed therein. FIG. 4A illustrates the result of evaluation of a mass absorption coefficient $\mu(2.3\ keV)$ for X-rays having energy of 2.3 keV and a mass absorption coefficient $\mu(4.5\ keV)$ for X-rays having energy of 4.5 keV regarding each sample. The value of each mass absorption coefficient increases with an increase in the percentage of ethanol. Next, a and b are calculated for each sample by assigning $\mu(2.3\ keV)$ and $\mu(4.5\ keV)$, which are obtained for each sample, respectively to $\ln(\mu)=a\times\ln(E)+b$. FIG. 4B illustrates the result of calculation of a and b for each sample from the value of the mass absorption coefficients illustrated in FIG. 4A. FIG. 5 is a characteristic diagram for illustrating the relation between constants a and b, which are calculated. In FIG. 5, a and b obtained for each sample are plotted in a coordinate space having an abscissa axis a and an ordinate axis b, and the relation between a and b can be approximated by a straight line as illustrated in FIG. 5. Accordingly, the following three formulas are satisfied for a sample having a mass absorption coefficient of μ, wherein g and h denote unknown constants.

$$\ln(\mu(2.3 \text{ keV})) = a \times \ln(2.3) + b \quad 5$$

$$\ln(\mu(4.5 \text{ keV})) = a \times \ln(4.5) + b$$

$$b = g \times a + h$$

When b is eliminated from the above three formulas, the following two formulas are obtained.

$$\ln(\mu(2.3 \text{ keV})) = a \times (\ln(2.3) + g) + h$$

$$\ln(\mu(4.5 \text{ keV})) = a \times (\ln(4.5) + g) + h$$

The following formula (7) is obtained from the above two formulas, and the following formula (8) can be obtained from the formula (7).

$$a = \frac{\ln(\mu(4.5 \text{ keV})) - h}{\ln(4.5) + g} \quad (7)$$

$$= \frac{\ln(\mu(2.3 \text{ keV})) - h}{\ln(2.3) + g}$$

$$\ln(\mu(2.3 \text{ keV})) = \frac{\ln(2.3) + g}{\ln(4.5) + g}(\ln(\mu(4.5 \text{ keV})) - h) + h \quad (8)$$

$$= \frac{\ln(2.3) + g}{\ln(4.5) + g}\ln(\mu(4.5 \text{ keV})) +$$

$$\frac{h(\ln(4.5) - \ln(2.3))}{\ln(4.5) + g}$$

$$= \gamma \times \ln(\mu(4.5 \text{ keV})) + \delta$$

wherein $$\gamma = \frac{\ln(2.3) + g}{\ln(4.5) + g}, \delta = \frac{h(\ln(4.5) - \ln(2.3))}{\ln(4.5) + g}$$

In the formula (8), γ and δ are respectively independent of the energy of X-rays and independent of the composition of a sample, and can be treated as constants. The above-described correction according to the composition of a sample for the value I, which is obtained by subtracting a background from the fluorescent X-ray intensity of sulfur included in a sample having a density of ρ and a mass absorption coefficient of μ, can be expressed in the expression (6). Regarding μ(2.3 keV) and $\mu_0$(2.3 keV) in the expression (6), the following formula (9) can be obtained from the formula (8).

$$\ln\left(\frac{\mu(2.3 \text{ keV})}{\mu_0(2.3 \text{ keV})}\right) = \gamma \times \ln(\mu(4.5 \text{ keV})) + \delta - \quad (9)$$

$$\{\gamma \times \ln(\mu_0(4.5 \text{ keV})) + \delta\}$$

$$= \gamma \times \{\ln(\mu(4.5 \text{ keV})) - \ln(\mu_0(4.5 \text{ keV}))\}$$

$$= \gamma \times \ln\left(\frac{\mu(4.5 \text{ keV})}{\mu_0(4.5 \text{ keV})}\right)$$

The following formula (10) is further obtained from the formula (9).

$$\frac{\mu(2.3 \text{ keV})}{\mu_0(2.3 \text{ keV})} = \left(\frac{\mu(4.5 \text{ keV})}{\mu_0(4.5 \text{ keV})}\right)^\gamma \quad (10)$$

The coefficient $(\rho\mu(2.3 \text{ keV})/\rho_0\mu_0(2.3 \text{ keV}))$ related to I in the expression (6) can be expressed by the following formula (11), by applying the formula (10).

$$\frac{\rho\mu(2.3 \text{ keV})}{\rho_0\mu_0(2.3 \text{ keV})} = \frac{\rho}{\rho_0}\left(\frac{\mu(4.5 \text{ keV})}{\mu_0(4.5 \text{ keV})}\right)^\gamma \quad (11)$$

$$= \left(\frac{\rho}{\rho_0}\right)^{1-\gamma} \cdot \left(\frac{\rho\mu(4.5 \text{ keV})}{\rho_0\mu_0(4.5 \text{ keV})}\right)^\gamma$$

In the formula (11), $(\rho/\rho_0)$ can be approximated by 1, since a density difference between samples is small. Moreover, $(\rho\mu(4.5 \text{ keV})/\rho_0\mu_0(4.5 \text{ keV}))$ included in the formula (11) becomes $(B_0/B)$ when a scattered X-ray intensity obtained from a reference sample is denoted by $B_0$, since a scattered X-ray intensity B is proportional to $1/(\rho \times \mu(4.5 \text{ keV}))$ as expressed in the formula (5). Accordingly, the expression (6) expressing the content of the correction according to the composition of a sample can be expressed by the following expression (12).

$$I \times \left(\frac{B_0}{B}\right)^\gamma \quad (12)$$

The correction corresponding to the composition of a sample can be performed for a value obtained by subtracting a background from a fluorescent X-ray intensity by using the expression (12). The constant γ included in the expression (12) can be calculated from the result of a fluorescent X-ray analysis of a plurality of standard samples, the concentrations of an object component (sulfur in the present embodiment) of which have known values that are not zero. A plurality of standard samples are required to have sulfur concentrations different from each other. A plurality of standard samples may be different from each other or the same in composition. Moreover, the reference sample may be included or not included in a plurality of standard samples. The number of a plurality of samples will be denoted by m, the sulfur concentration of a k-th standard sample will be denoted by $C_k$, a value obtained by subtracting a background from the fluorescent X-ray intensity of sulfur will be denoted by $I_k$, and a scattered X-ray intensity will be denoted by $B_k$. The following formula (13) is satisfied using a constant D on the basis of the expression (12), when assuming that the concentration of sulfur in a sample is proportional to the fluorescent X-ray intensity of sulfur obtained by subtracting a background.

$$C_k = I_k \times \left(\frac{B_0}{B_k}\right)^\gamma \times D \quad (13)$$

The formula (13) can be transformed into the following formula (14) by logarithmic expression of both side of the formula (13).

$$\ln(C_k) = \ln(I_k) + \gamma \times \ln\left(\frac{B_0}{B_k}\right) + \ln(D) \quad (14)$$

$$\ln(C_k) - \ln(I_k) = \gamma \times \ln\left(\frac{B_0}{B_k}\right) + \ln(D)$$

The formula (14) takes the form of a linear formula y=γx+d when y=ln($C_k$)−ln($I_k$), x=ln($B_0/B_k$) and d=ln(D) are satisfied in the formula (14). The constant γ can be calculated by calculating the formula (14) for each of the standard samples, the number of which is m, and applying the method of least squares to the calculated formulas (14), the number of which is m. The expression (12) wherein γ is set is a correction formula according to the present invention. By using the expression (12), the correction corresponding to the composition of a sample can be performed for a value obtained by subtracting a background from a fluorescent X-ray intensity.

Since the effect of the composition of a sample is removed by the correction according to the present invention, it is possible to obtain a calibration curve, which can be applied to a sample having any composition, from a value obtained after performing the correction for a fluorescent X-ray intensity obtained by subtracting a background. A calibration curve can be created from the result of a fluorescent X-ray analysis of a plurality of standard samples, the concentrations of an object component (sulfur in the present embodiment) of which have known values. A standard sample to be used for creating a calibration curve may be the same as or different from a standard sample used for calculating a correction parameter γ. A plurality of standard samples may be different from one another or the same in composition. Moreover, the reference sample may be included or not included in a plurality of standard samples. The number of a plurality of standard samples will be denoted by n, and a value, which is obtained after subtracting a background from a fluorescent X-ray intensity of sulfur included in a k-th standard sample and performing the correction, will be denoted by $X_k$. When the relation between a sulfur concentration C and a value X obtained after performing the correction for the fluorescent X-ray intensity obtained by subtracting a background can be expressed by a linear formula, a calibration curve can be expressed by the following formula (15) using constants p and q, and the following formula (16) is satisfied for the k-th standard sample.

$$C = p \times X + q \quad (15)$$

$$C_k = p \times X_k + q \quad (16)$$

The constants p and q can be calculated by calculating the formula (16) for each of the standard samples, the number of which is m, and applying the method of least squares to the calculated formulas (16), the number of which is m. The formula (15) in which the values of p and q are set is a calibration curve. When a fluorescent X-ray analysis is made for an arbitrary sample, it becomes possible to calculate the concentration C of sulfur in a sample by calculating the value X obtained after performing the correction for the fluorescent X-ray intensity of sulfur obtained by subtracting a background on the basis of the result of the fluorescent X-ray analysis and assigning the value X to the formula (15) expressing the calibration curve. It is to be noted that a calibration curve is not limited to a linear formula and may be created as another relation formula such as a quadratic formula.

Next, processes for a concentration measuring method to be performed by a fluorescent X-ray spectrometer of the present invention will be explained. A fluorescent X-ray spectrometer can execute: a calibration process for deciding constants α, β and γ; a calibration curve creating process for creating a calibration curve; and a concentration measuring process for measuring the concentration of an object component (sulfur in the present embodiment) in an arbitrary sample.

Figure 6:
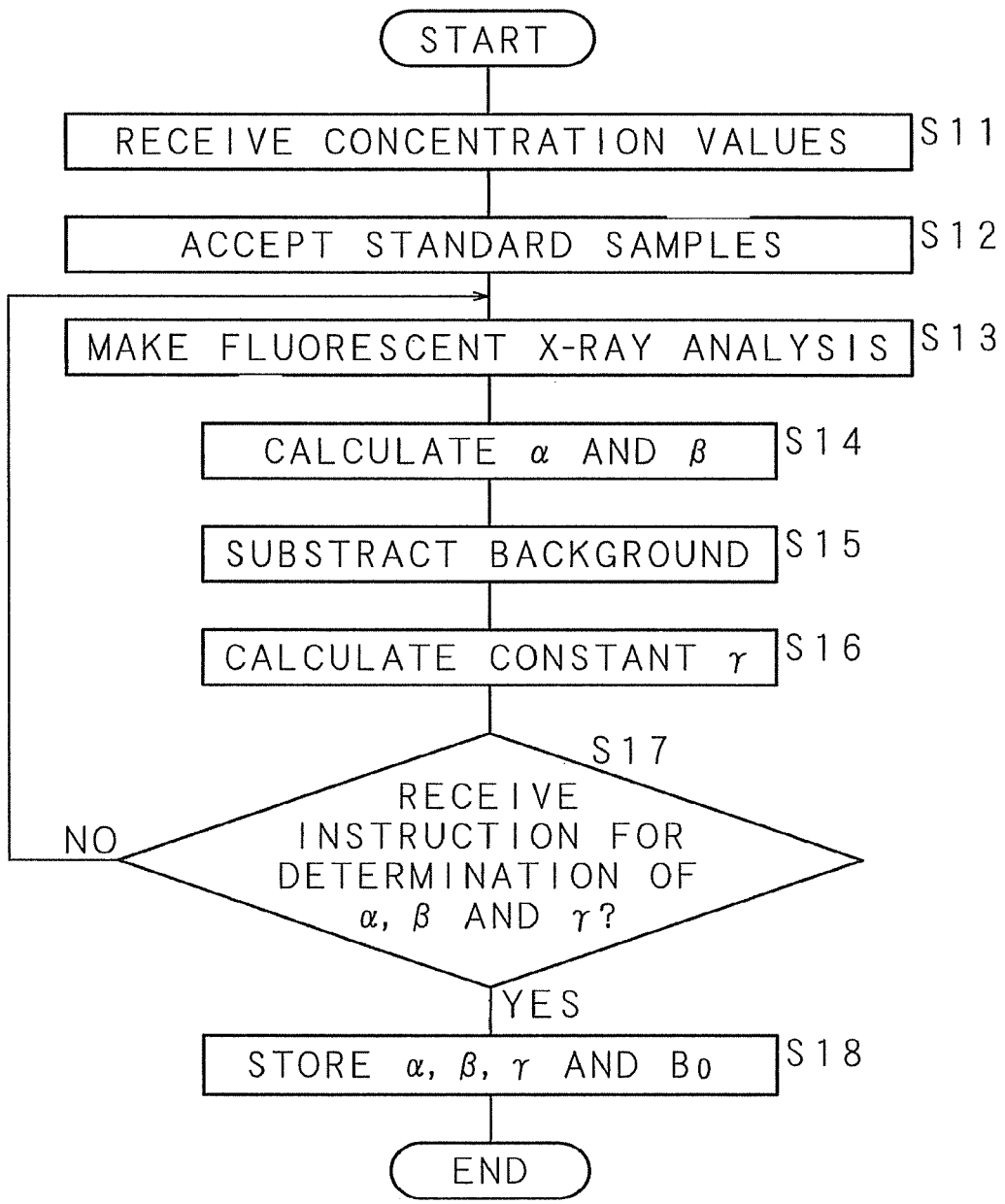
FIG. 6 is a flow chart for illustrating the procedure of a calibration process to be executed by a fluorescent X-ray spectrometer.

FIG. 6 is a flow chart for illustrating the procedure of a calibration process to be executed by a fluorescent X-ray spectrometer. The fluorescent X-ray spectrometer starts a calibration process when the user operates the operation unit 64 to enter an instruction for starting the calibration process. First, the fluorescent X-ray spectrometer receives concentration values of sulfur included in a plurality of standard samples to be used for calculating α, β and γ (S11). In the step S11, the processing unit 62 displays an entry screen to be used for entering a concentration value at the display unit 65 and the user enters a concentration value through the operation unit 64. With such a manner, the fluorescent X-ray spectrometer receives a concentration value of sulfur for each standard sample. At least two or more standard samples, the concentration values of which are zero, and at least two or more standard samples, the concentration values of which are not zero, are required as standard samples for the calibration process. Next, the fluorescent X-ray spectrometer accepts a plurality of standard samples when the user places a plurality of sample cells 3, in which a plurality of standard samples are respectively encapsulated, inside the cover 2 (S12). A turn table, on which a plurality of sample cells 3 can be placed, is provided inside the cover 2 of the fluorescent X-ray spectrometer. The step S12 is achieved when the user places a sample cell 3, in which a sample having the entered concentration value is encapsulated, on the turn table.

Next, the fluorescent X-ray spectrometer actuates the turn table to place the sample cell 3 at a position to be irradiated with primary X-rays from the X-ray tube 4 and irradiates the sample in the sample cell 3 with primary X-rays from the X-ray tube 4. The fluorescent X-ray spectrometer then detects secondary X-rays with the X-ray detector 5 and analyzes an output of the X-ray detector 5 with the analyzing unit 61 to acquire a spectrum. With such a manner, the fluorescent X-ray spectrometer makes a fluorescent X-ray analysis of a standard sample (S13). In the step S13, the fluorescent X-ray spectrometer performs a process for acquiring a spectrum for each of the plurality of standard samples. The processing unit 62 acquires a fluorescent X-ray intensity S of sulfur and a scattered X-ray intensity B on the basis of spectrums related to two standard samples, the concentration values of which are zero, of spectrums acquired for the respective standard samples. The processing unit 62 calculates α and β by assigning the fluorescent X-ray intensity S of sulfur and the scattered X-ray intensity B, which have been acquired, to the formulas (2) and (3) (S14). It is to be noted that α and β may be calculated using the method of least squares on the basis of spectrums related to three or more standard samples, the concentration values of which are zero, as described above.

Next, the processing unit 62 obtains a fluorescent X-ray intensity S of sulfur and a scattered X-ray intensity B on the basis of a spectrum related to each standard sample. The processing unit 62 subtracts a background from the fluorescent X-ray intensity of sulfur by assigning the fluorescent X-ray intensity S of sulfur and the scattered X-ray intensity B, which have been obtained, and α and β calculated at the step S14 to the formula (1) (S15). Next, the processing unit 62 calculates a constant γ on the basis of the fluorescent X-ray intensity of sulfur obtained by subtracting a background for each standard sample (S16). In the step S16, the processing unit 62 sets one of the plurality of standard samples as a reference sample and assigns a concentration value, the fluorescent X-ray intensity obtained by subtracting a background, a scattered X-ray intensity and a scattered X-ray intensity of a reference sample to the formula (14) for each standard sample. The processing unit 62 calculates the value γ by applying the method of least squares to the plurality of formulas (14), to which the values have been assigned.

Next, the processing unit 62 displays the calculated values of α, β and γ at the display unit 65 and waits for reception of an instruction for determination to be given by the user, who has checked the values, through the operation of the operation unit 64 (S17). When the processing unit 62 has not received an instruction for determination since the processing unit 62 has received an instruction for remeasurement or the like (S17: NO), the fluorescent X-ray spectrometer returns the process to the step S13 and makes a fluorescent X-ray analysis of each standard sample again. When the processing unit 62 has received an instruction for determination (S17: YES), the processing unit 62 stores the calculated α, β and γ and the scattered X-ray intensity $B_0$ of a reference sample used for calculation in the storage unit 63 (S18). The processing unit 62 terminates the calibration process after the step S18. It is to be noted that a fluorescent X-ray spectrometer of an embodiment may be provided with no turn table, and reception of a concentration value, acceptance of a standard sample and a series of operations of the fluorescent X-ray analysis may be executed one by one for each standard sample. A subtraction formula is stored when α and β are stored in the storage unit 63, and a correction formula is stored when γ and $B_0$ are stored in the storage unit 63.

Figure 7:
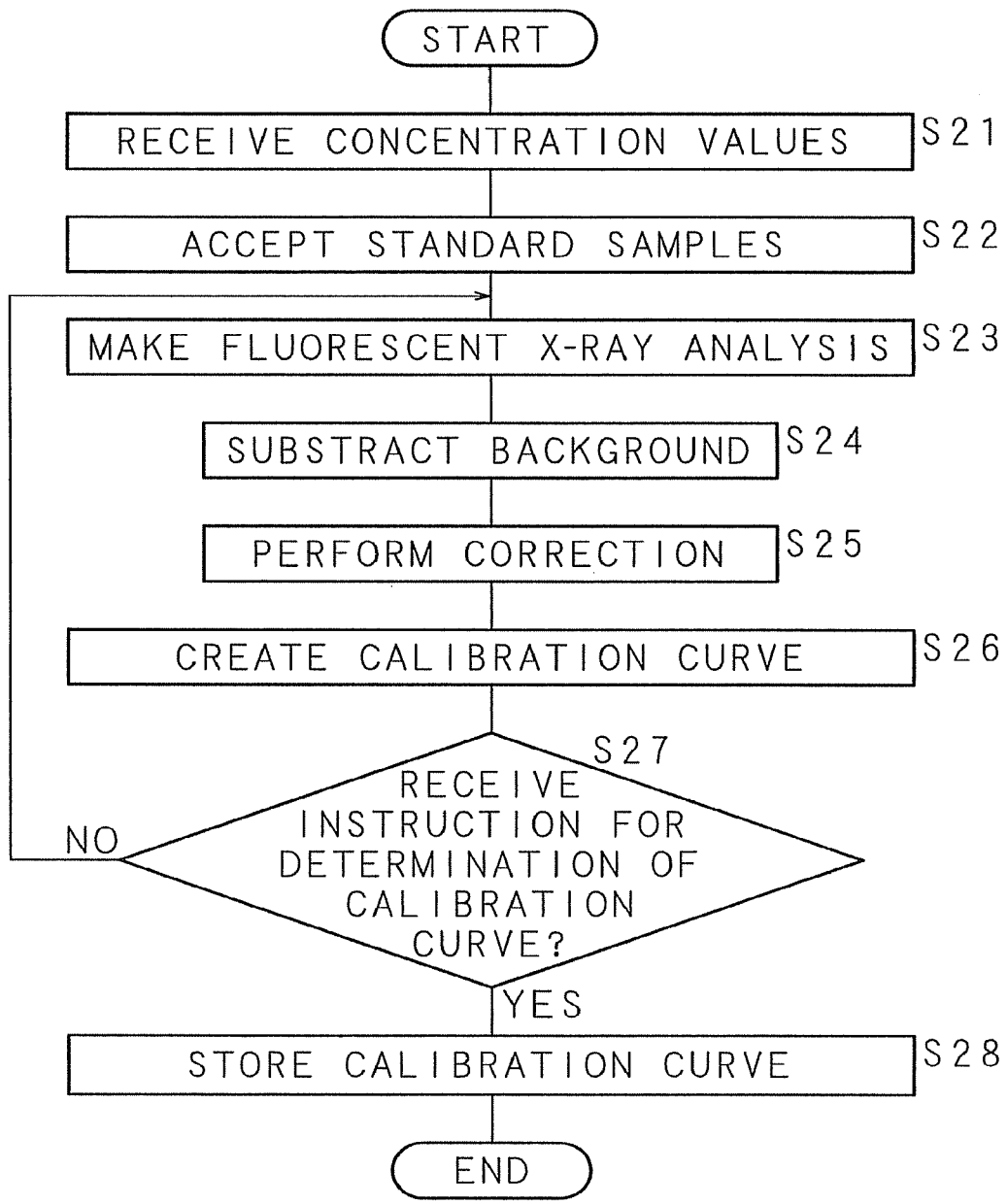
FIG. 7 is a flow chart for illustrating the procedure of a calibration curve creating process to be executed by a fluorescent X-ray spectrometer.

FIG. 7 is a flow chart for illustrating the procedure of a calibration curve creating process to be executed by a fluorescent X-ray spectrometer. The fluorescent X-ray spectrometer starts a calibration curve creating process when the user operates the operation unit 64 to enter an instruction, for starting the calibration curve creating process. First, the fluorescent X-ray spectrometer receives concentration values of sulfur included in a plurality of standard samples to be used for creating a calibration curve (S21). At least two or more standard samples, the concentration values of which are different from each other, are used as standard samples for the calibration curve creating process. It is to be noted that a fluorescent X-ray spectrometer of an embodiment may be constructed to allow the user to give an instruction for selecting a function form of a calibration curve, such as a linear formula or a quadratic formula, at the step S21. Next, the fluorescent X-ray spectrometer accepts a plurality of standard samples having the received concentration values (S22).

Next, the fluorescent X-ray spectrometer makes a fluorescent X-ray analysis of each of a plurality of standard samples (S23). The processing unit 62 obtains a fluorescent X-ray intensity S of sulfur and a scattered X-ray intensity B on the basis of a spectrum acquired for each standard sample. The processing unit 62 subtracts a background from the fluorescent X-ray intensity of sulfur by assigning S and B, which have been obtained, and α and β, which are stored in the storage unit 63, to the formula (1) (S24). Next, the processing unit 62 performs a correction corresponding to the composition of each standard sample for the value I obtained by subtracting a background from the fluorescent X-ray intensity of sulfur calculated for each standard sample (S25). In the step S25, the processing unit 62 performs the correction by assigning I and B, and γ and $B_0$, which are stored in the storage unit 63, to the expression (12). Next, the processing unit 62 creates a calibration curve on the basis of a value obtained after subtracting a background from a fluorescent X-ray intensity of sulfur included in each standard sample and performing the correction (S26). In the step S26, the processing unit 62 assigns a concentration value and a value, which is obtained after performing the correction for the fluorescent X-ray intensity obtained by subtracting a background, to the formula (16) for each standard sample. The processing unit 62 applies the method of least squares to a plurality of formulas (16), to which values have been assigned, to obtain the values of p and q. With such a manner, the processing unit 62 creates a calibration curve. It is to be noted that a calibration curve other than a linear formula can be also created as described above.

Next, the processing unit 62 displays a screen for the user to check the created calibration curve and waits for reception of an instruction for determination to be given by the user, who has checked the calibration curve, through operation of the operation unit 64 (S27). In the step S27, the processing unit 62 displays a screen for the user to check a calibration curve by: a method of displaying the obtained values of p and q at the display unit 65; a method of displaying a graph illustrating the line shape of the calibration curve at the display unit 65; or the like. When the processing unit 62 has not received an instruction for determination since the processing unit 62 has received an instruction for remeasurement or the like (S27: NO), the fluorescent X-ray spectrometer returns the process to the step S23 and makes a fluorescent X-ray analysis of each standard sample again. When the processing unit 62 has received an instruction for determination (S27: YES), the processing unit 62 stores the obtained p and q in the storage unit 63 so as to store the calibration curve in the storage unit 63 (S28). The processing unit 62 terminates the calibration curve creating process after the step S28. It is to be noted that the processing unit 62 may store a calibration curve itself in the storage unit 63 in the step S28 by, for example, a method of storing a numerical value table illustrating the relation between a concentration value and a value obtained after performing the correction for the fluorescent X-ray intensity obtained by subtracting a background on a calibration curve.

A calibration process and a calibration curve creating process are required to be executed at least one time before making an analysis of an arbitrary sample using a fluorescent X-ray spectrometer. It is preferable to execute a calibration process and a calibration curve creating process on a regular basis at intervals, e.g. once a month, in order to assure the precision of concentration measurement. Moreover, it is also preferable to execute a calibration process and a calibration curve creating process when the use environment of a fluorescent X-ray spectrometer is changed by, for example, a change in the installation site of the fluorescent X-ray spectrometer.

Figure 8:
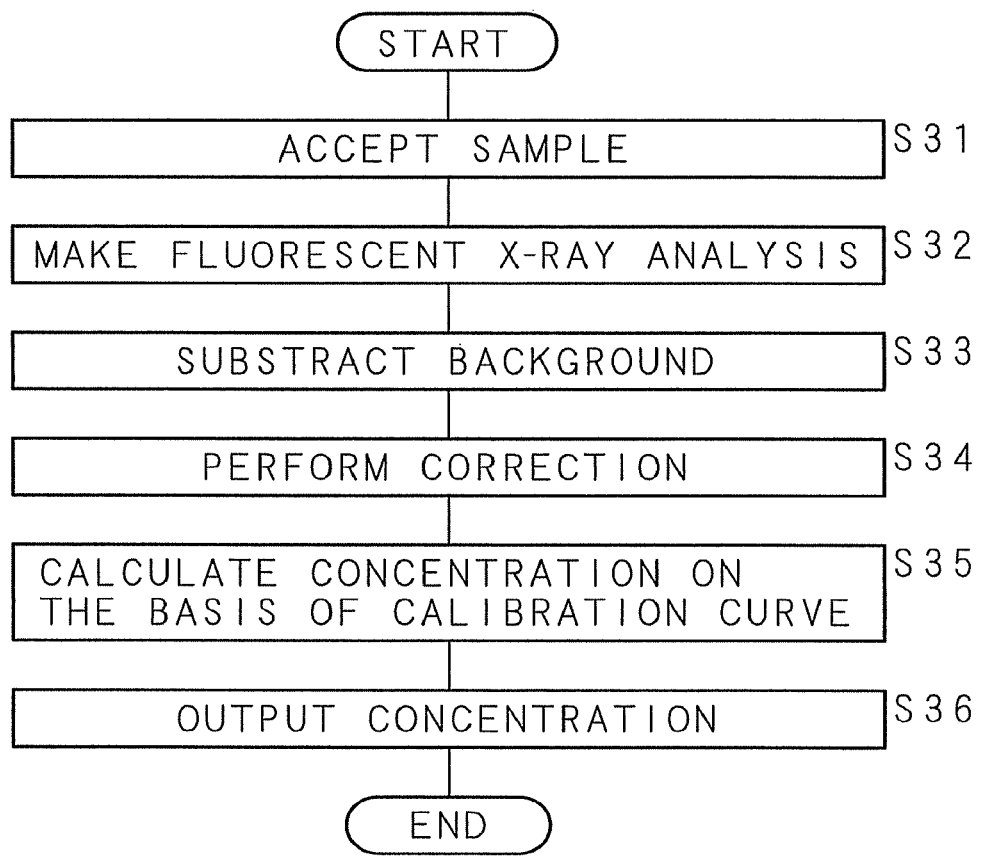
FIG. 8 is a flow chart for illustrating the procedure of a concentration measuring process to be executed by a fluorescent X-ray spectrometer.

FIG. 8 is a flow chart for illustrating the procedure of a concentration measuring process to be executed by a fluorescent X-ray spectrometer. The fluorescent X-ray spectrometer starts a concentration measuring process when the user operates the operation unit 64 to enter an instruction for starting concentration measurement. The fluorescent X-ray spectrometer accepts a sample when the user places a sample cell 3, in which a sample including an object component (sulfur in the present embodiment) is capsulated, inside the cover 2 (S31). Next, the fluorescent X-ray spectrometer irradiates the sample in the sample cell 3 with primary X-rays from the X-ray tube 4 and detects secondary X-rays with the X-ray detector 5. The fluorescent X-ray spectrometer analyzes an output of the X-ray detector 5 with the analyzing unit 61 to acquire a spectrum. With such a manner, the fluorescent X-ray spectrometer makes a fluorescent X-ray analysis of the sample (S32). The processing unit 62 obtains a fluorescent X-ray intensity S of sulfur and a scattered X-ray intensity B from the acquired spectrum. The processing unit 62 subtracts a background from the fluorescent X-ray intensity of sulfur by assigning S and B, which have been obtained, and α and β, which are stored in the storage unit 63, to the formula (1) (S33).

Next, the processing unit 62 assigns a value I, which is obtained by subtracting a background from the fluorescent X-ray intensity of sulfur, and B, and $\gamma$ and $B_0$ stored in the storage unit 63 to the expression (12). With such a manner, the processing unit 62 performs a correction corresponding to the composition of each standard sample for the fluorescent X-ray intensity of sulfur obtained by subtracting a background (S34). Next, the processing unit 62 finds a concentration value, which corresponds to a value obtained after subtracting a background from the fluorescent X-ray intensity of sulfur included in a sample and performing the correction, on a calibration curve stored in the storage unit 63. With such a manner, the processing unit 62 calculates the sulfur concentration on the basis of the calibration curve (S35). Next, the processing unit 62 outputs the measured concentration by displaying the calculated value of the concentration at the display unit 65 (S36). The processing unit 62 terminates the concentration measuring process after the step S36. It is to be noted that a fluorescent X-ray spectrometer of an embodiment may output the measured concentration using a personal computer (PC), a printer or the like, which is not illustrated in the figures.

As described above in detail, in the present invention, a fluorescent X-ray analysis is made for a sample such as a liquid fuel including sulfur, and a background related to scattered X-rays and a system peak is subtracted from a fluorescent X-ray intensity of sulfur to be obtained from a spectrum acquired by the fluorescent X-ray analysis. Furthermore, in the present invention, a correction corresponding to the composition of a sample is performed for the fluorescent X-ray intensity obtained by subtracting a background, and the concentration of sulfur in the sample is calculated on the basis of a calibration curve representing the relation between a value obtained after performing the correction and the sulfur concentration. The concentration of sulfur included even in a sample having a low sulfur concentration can be measured by subtracting a background from the fluorescent X-ray intensity of sulfur. Moreover, a corrected value corresponding to the sulfur concentration can be obtained independently of the composition of a sample, by performing a correction corresponding to the composition of the sample for the fluorescent X-ray intensity obtained by subtracting a background. Accordingly, it is unnecessary to create a calibration curve for each sample, the composition of which is different, and it is possible to make a high-precision measurement of the concentration of sulfur in a sample having any composition by a fluorescent X-ray analysis. Especially, the present invention makes it possible to make a high-precision measurement of the concentration of sulfur, which is a hazardous component, for various liquid fuels including a new type of liquid fuel such as ethanol or bio gasoline, and the present invention can be used for reducing the concentration of sulfur included in a liquid fuel.

It is to be noted that an object component is not limited to sulfur, though an example in which sulfur is used as an object component has been described in the present embodiment. The present invention can be used for measuring the concentration of any component, for which fluorescent X-rays can be measured. Moreover, the present invention is not limited to the present embodiment wherein a sample is a liquid fuel such as a diesel fuel. With the present invention, it is possible to measure the concentration of an object component in a sample having any composition, as long as the sample has a composition containing carbon and/or oxygen as a major ingredient. It is to be noted that it is possible to measure the concentration of an object component in a sample other than a sample having a composition containing carbon and/or oxygen as a major ingredient, as long as the composition of the sample has a linear relation between the energy of X-rays and the mass absorption coefficient in a double logarithmic chart.

Moreover, the present invention is not limited to the present embodiment wherein all processes up to calculation of a concentration are executed by a fluorescent X-ray spectrometer. In a concentration measuring method of the present invention, a fluorescent X-ray spectrometer may execute only the processes up to a fluorescent X-ray analysis, and subsequent processes may be executed by a computing device such as a PC provided outside the fluorescent X-ray spectrometer. Said processes include a process for obtaining a subtraction formula and a correction formula from a spectrum acquired by a fluorescent X-ray analysis and a process for calculating the concentration of an object component.

As this description may be embodied in several forms without departing from the spirit of essential characteristics thereof, the present embodiment is therefore illustrative and not restrictive, since the scope is defined by the appended claims rather than by the description preceding them, and all changes that fall within metes and bounds of the claims, or equivalence of such metes and bounds thereof are therefore intended to be embraced by the claims.

What is claimed is:

1. A concentration measuring method for measuring a concentration of an object component in a sample from a fluorescent X-ray intensity by means of a fluorescent X-ray spectrometer, comprising steps of:

acquiring spectrums of secondary X-rays generated by irradiating a plurality of standard samples, concentrations of the object component of which are zero and compositions of which are different from each other, with primary X-rays;

setting a subtraction formula by calculating constants $\alpha$ and $\beta$ according to a plurality of formulas obtained by setting I=0 and assigning S and B, which are obtained from the spectrums acquired for a plurality of standard samples, to a subtraction formula I=S−α∆B−β (wherein I: a fluorescent X-ray intensity obtained by subtracting the background, S: a fluorescent X-ray intensity of the object component obtained from a spectrum, α and β: constants, and B: a scattered X-ray intensity obtained from a spectrum) for subtracting the background from the fluorescent X-ray intensity of the object component, which is obtained from a spectrum;

irradiating the sample with primary X-rays;

acquiring a spectrum of secondary X-rays generated from the sample;

obtaining a fluorescent X-ray intensity of the object component included in the sample from the acquired spectrum;

subtracting the background from the fluorescent X-ray intensity of the object component by assigning S and B, which are obtained from an acquired spectrum, to a subtraction formula in which calculated values are set as α and β;

performing a correction corresponding to a composition of the sample for the fluorescent X-ray intensity obtained by subtracting the background; and calculating a concentration of the object component in the sample on the basis of a calibration curve representing a relation between a concentration of the object component and a value obtained after performing the correction for the fluorescent X-ray intensity obtained by subtracting the background.

2. The concentration measuring method according to claim 1, comprising steps of:
acquiring spectrums of secondary X-rays generated from a plurality of standard samples, concentrations of the object component of which have known values that are not zero;
subtracting the background from fluorescent X-ray intensities of the object component, which are obtained from the spectrums acquired for a plurality of standard samples; and
setting a correction formula for performing the correction, on the basis of a relation between concentrations of the object component related to a plurality of standard samples and fluorescent X-ray intensities obtained by subtracting the background.

3. The concentration measuring method according to claim 2, comprising steps of:
setting a correction formula $I \times (B_0/B)^\gamma$ by calculating a constant $\gamma$ according to a plurality of formulas obtained by assigning $I_k$, $B_0$ and $B_k$ to a relation formula (wherein $I_k$: a value obtained by subtracting the background from a fluorescent X-ray intensity of an object component obtained from a spectrum related to a k-th standard sample, $B_0$: a scattered X-ray intensity obtained from a spectrum related to a specific reference sample to be a reference of a fluorescent X-ray intensity, $B_k$: a scattered X-ray intensity obtained from a spectrum related to the k-th standard sample, and $\gamma$: a constant) expressing that a concentration $C_k$ of the object component related to the k-th standard sample is proportional to $I_k \times (B_0/B_k)^\gamma$; and
performing the correction by assigning I and B to a correction formula in which a calculated value is set as $\gamma$.

4. The concentration measuring method according to claim 1, comprising steps of:
acquiring spectrums of secondary X-rays generated from a plurality of standard samples, concentrations of the object component of which have known values that are different from each other;
subtracting the background from fluorescent X-ray intensities of the object component obtained from a plurality of acquired spectrums;
performing the correction for values obtained by subtracting the background from fluorescent X-ray intensities related to a plurality of standard samples; and
obtaining a calibration curve representing a relation between a concentration of the object component in the sample and a value obtained after performing the correction for the fluorescent X-ray intensity obtained by subtracting the background, from concentrations of the object component related to a plurality of standard samples and values obtained after performing the correction for values obtained by subtracting the background from fluorescent X-ray intensities related to a plurality of standard samples.

5. A fluorescent X-ray spectrometer for calculating a concentration of an object component in a sample from a fluorescent X-ray intensity, comprising:
a first acquiring unit for acquiring spectrums of secondary X-rays generated by irradiating a plurality of standard samples, concentrations of the object component of which are zero and compositions of which are different from each other, with primary X-rays;
a setting unit for setting a subtraction formula by calculating constants $\alpha$ and $\beta$ according to a plurality of formulas obtained by setting I=0 and assigning S and B, which are obtained from the spectrums acquired for a plurality of standard samples, to a subtraction formula $I=S-\alpha \times B-\beta$ (wherein I: a fluorescent X-ray intensity obtained by subtracting the background, S: a fluorescent X-ray intensity of the object component obtained from a spectrum, $\alpha$ and $\beta$: constants, and B: a scattered X-ray intensity obtained from a spectrum) for subtracting the background from the fluorescent X-ray intensity of the object component, which is obtained from a spectrum;
an irradiating unit for irradiating the sample with primary X-rays;
a second acquiring unit for acquiring a spectrum of secondary X-rays generated from the sample;
an obtaining unit for obtaining a fluorescent X-ray intensity of the object component included in the sample from the spectrum;
a subtraction formula storing unit for storing the subtraction formula set by the setting unit;
a correction formula storing unit for storing a correction formula for performing a correction corresponding to a composition of the sample for the fluorescent X-ray intensity obtained by subtracting the background;
a calibration curve storing unit for storing a calibration curve representing a relation between a concentration of the object component and a value obtained after performing the correction for the fluorescent X-ray intensity obtained by subtracting the background;
a subtracting unit for subtracting the background from the fluorescent X-ray intensity of the object component, which is obtained by the obtaining unit from the spectrum acquired by the second acquiring unit, using the subtraction formula;
a correction unit for performing the correction for the fluorescent X-ray intensity, which is obtained by subtracting the background, using the correction formula; and
a concentration calculating unit for calculating a concentration of the object component in the sample on the basis of the calibration curve.

* * * * *